United States Patent
Hidaka et al.

(10) Patent No.: US 11,540,705 B2
(45) Date of Patent: Jan. 3, 2023

(54) WELDED STRUCTURE OF TUBULAR MEMBER AND BENDING DEVICE

(71) Applicant: OLYMPUS CORPORATION, Tokyo (JP)

(72) Inventors: Takeshi Hidaka, Hachioji (JP); Jumpei Otake, Kunitachi (JP); Harutaka Kondo, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 747 days.

(21) Appl. No.: 16/538,973

(22) Filed: Aug. 13, 2019

(65) Prior Publication Data

US 2020/0000313 A1 Jan. 2, 2020

Related U.S. Application Data

(63) Continuation of application No. PCT/JP2018/008508, filed on Mar. 6, 2018.

(30) Foreign Application Priority Data

Apr. 4, 2017 (JP) .................................. 2017-074588

(51) Int. Cl.
    *A61B 1/008* (2006.01)
    *B23K 26/21* (2014.01)
    (Continued)

(52) U.S. Cl.
    CPC .............. *A61B 1/008* (2013.01); *A61B 34/71* (2016.02); *B23K 26/21* (2015.10);
    (Continued)

(58) Field of Classification Search
    CPC .................... A61B 1/008; A61B 34/71; A61B 2017/00314; A61B 2017/00327;
    (Continued)

(56) References Cited

U.S. PATENT DOCUMENTS

| 2015/0087910 | A1 | 3/2015 | Okazaki |
| 2016/0121422 | A1* | 5/2016 | Si .......................... B23K 9/167 |
| | | | 219/74 |

FOREIGN PATENT DOCUMENTS

| JP | H05-003852 A | 1/1993 |
| JP | H06-64240 B2 | 8/1994 |

(Continued)

OTHER PUBLICATIONS

International Search Report dated Jan. 5, 2018, issued in PCT/JP2018/008508.
English Abstract of JP S60-102607A dated Jun. 6, 1985.

*Primary Examiner* — Gary Jackson
*Assistant Examiner* — Sebastian X Lukjan
(74) *Attorney, Agent, or Firm* — Scully, Scott, Murphy & Presser, P.C.

(57) ABSTRACT

A welded structure, in which a second tubular member is welded to an inner circumference of a first tubular member made of metal, the second tubular member being made of metal and having an outer diameter smaller than an inner diameter of the first tubular member, includes welded portions at which a portion of the first tubular member and a portion of the second tubular member are melted and solidified, a surface melted and solidified from an inner circumferential surface side of the first tubular member toward an end surface of the second tubular member forms a smoothly-continuous curved surface, and the first and the second tubular members are bonded to each other. A portion of each of the welded portions is located on an outside of a projection region obtained by projecting the second tubular member onto an outer surface of the first tubular member.

14 Claims, 7 Drawing Sheets

(51) Int. Cl.
  *G02B 23/24* (2006.01)
  *A61B 17/00* (2006.01)
  *A61B 34/00* (2016.01)

(52) U.S. Cl.
  CPC ............... *A61B 2017/00314* (2013.01); *A61B 2017/00327* (2013.01); *G02B 23/24* (2013.01)

(58) Field of Classification Search
  CPC .... A61B 1/0055; A61B 1/0057; B23K 26/21; B23K 26/22; G02B 23/24; G02B 23/2484
  See application file for complete search history.

(56) References Cited

FOREIGN PATENT DOCUMENTS

| | | | |
|---|---|---|---|
| JP | H08-146306 A | 6/1996 | |
| JP | H09-323174 A | 12/1997 | |
| WO | WO-2005048862 A2 * | 6/2005 | ............. A61B 18/14 |
| WO | WO-2013131187 A1 * | 9/2013 | ........... A61N 1/0551 |
| WO | WO 2014/192446 A1 | 12/2014 | |

* cited by examiner

WELDED STRUCTURE OF TUBULAR MEMBER AND BENDING DEVICE

This application is a continuation of PCT International Application No. PCT/JP2018/008508 filed on Mar. 6, 2018, which designates the United States, incorporated herein by reference, and which claims the benefit of priority from Japanese Patent Application No. 2017-074588, filed on Apr. 4, 2017, incorporated herein by reference.

BACKGROUND

The present disclosure relates to a welded structure of a tubular member, and a bending device.

In the related art, a bending unit configured to bend to enable a change of a direction of a distal end of an endoscope or a distal end of a manipulator is provided in a distal end portion of the endoscope or a distal end portion of the manipulator. The bending unit is constituted by a plurality of tubular joint rings. An operation wire used for operating the bending unit is inserted into the plurality of joint rings. A wire holder into which the operation wire is inserted is fixed to each of inner circumferential surfaces of at least some of the plurality of joint rings (for example, see JP H06-64240 B and JP H08-146306 A).

The wire holder is fixed to the joint ring by welding. In JP H06-64240 B, the wire holder is fixed to the joint ring in a manner that an outer circumferential surface of the wire holder is fit to the inner circumferential surface of the joint ring, and a portion at which the joint ring and the wire holder are joined to each other at both end portions of the operation wire in an insertion direction is welded. In JP H08-146306 A, a welded portion is formed at a central portion of a projection region obtained by projecting the wire holder onto the outer circumferential surface of the joint ring, and an excess-welded portion is provided at a position adjacent to the welded portion in a circumferential direction of the joint ring, and thus fixation strength between the joint ring and the wire holder increases.

SUMMARY

A welded structure of a tubular member, in which a second tubular member is welded to an inner circumference of a first tubular member made of metal, the second tubular member being made of metal and having an outer diameter smaller than an inner diameter of the first tubular member, includes: a plurality of welded portions at which a portion of the first tubular member and a portion of the second tubular member are melted and solidified, a surface melted and solidified from an inner circumferential surface side of the first tubular member toward an end surface of the second tubular member forms a smoothly-continuous curved surface, and the first tubular member and the second tubular member are bonded to each other, wherein a portion of each of the welded portions is located on an outside of a projection region obtained by projecting the second tubular member onto an outer surface of the first tubular member.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, forms for embodying the present disclosure (referred to as "embodiments" below) will be described in detail with reference to the accompanying drawings. The drawings are schematic, and the dimensional relationships and ratios of the components are different from those in practice. Parts having dimensional relationships and ratios of components different from each other in the drawings are provided.

Embodiment

Figure 1:
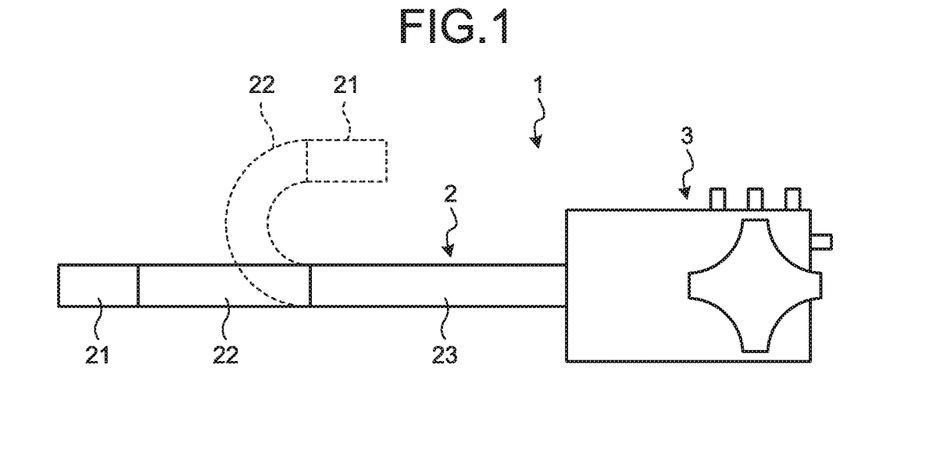
FIG. 1 is a schematic diagram illustrating a configuration of an endoscope according to an embodiment.

FIG. 1 is a schematic diagram illustrating a configuration of an endoscope according to an embodiment. An endoscope 1 illustrated in FIG. 1 has an elongated shape and includes an insertion portion 2 and an operating unit 3. The insertion portion 2 has an elongated shape and is inserted into a subject. The operating unit 3 is connected to a proximal end of the insertion portion 2 and receives an input of various operation signals. A universal cord is provided in the operating unit 3. The universal cord extends from the operating unit 3 in a direction different from a direction in which the insertion portion 2 extends. In the universal cord, various cables connected to a processing device are mounted. An image signal acquired by the endoscope 1 is transmitted to the processing device via the universal cord, and thus a display image is generated in the processing device.

The insertion portion 2 includes a distal end portion 21, a flexible bending unit 22, and a flexible tube portion 23. At the distal end portion 21, an imaging unit that generates an image signal by receiving light and performing photoelectric conversion. The flexible bending unit 22 is constituted by a plurality of joint rings. The flexible tube portion 23 is connected to the proximal end of the bending unit 22, has flexibility, and is long.

For example, a curved knob, a treatment tool insertion unit, and a plurality of switches are provided in the operating unit 3. The curved knob is used for bending the bending unit 22 in a vertical direction and a horizontal direction. The treatment tool insertion unit inserts a treatment tool such as biopsy forceps, an electric knife, and an inspection probe, into a subject. The switches correspond to an operation input unit that inputs an operation instruction signal from peripheral devices such as air supply unit, water supply unit, and screen display control.

Figure 2:
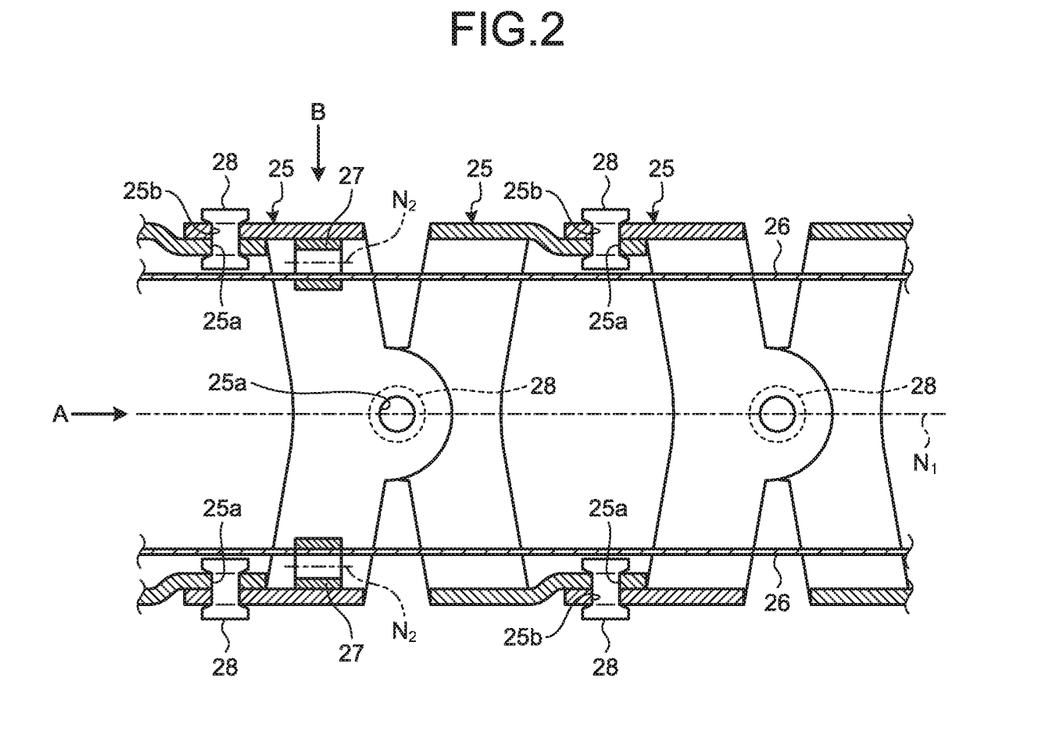
FIG. 2 is a partial sectional view illustrating a configuration of main components of the endoscope according to the embodiment.
Figure 3:
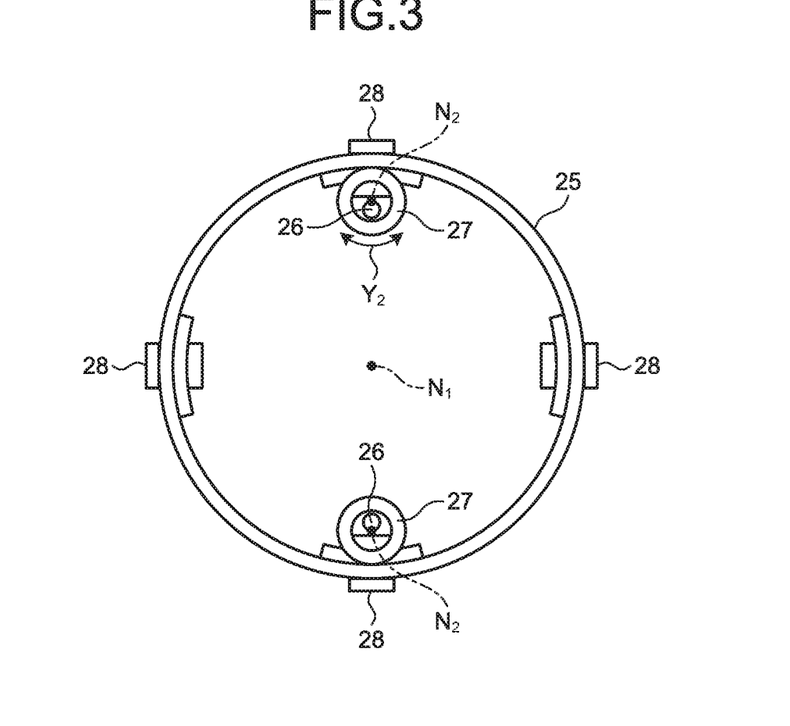
FIG. 3 is a diagram illustrating a configuration of a joint ring and a wire holder in the endoscope, which corresponds to a direction indicated by an arrow A illustrated in FIG. 2.

FIG. 2 is a partial sectional view illustrating a configuration of main components of the endoscope according to the embodiment. FIG. 3 is a diagram illustrating a configuration of a joint ring and a wire holder in the endoscope, which corresponds to a direction indicated by an arrow A illustrated in FIG. 2. In the bending unit 22, the plurality of joint rings 25 is arranged in a longitudinal direction of the insertion portion 2. The plurality of joint rings 25 is formed with metal, and each of the joint rings 25 has a substantially the same shape.

Figure 4:
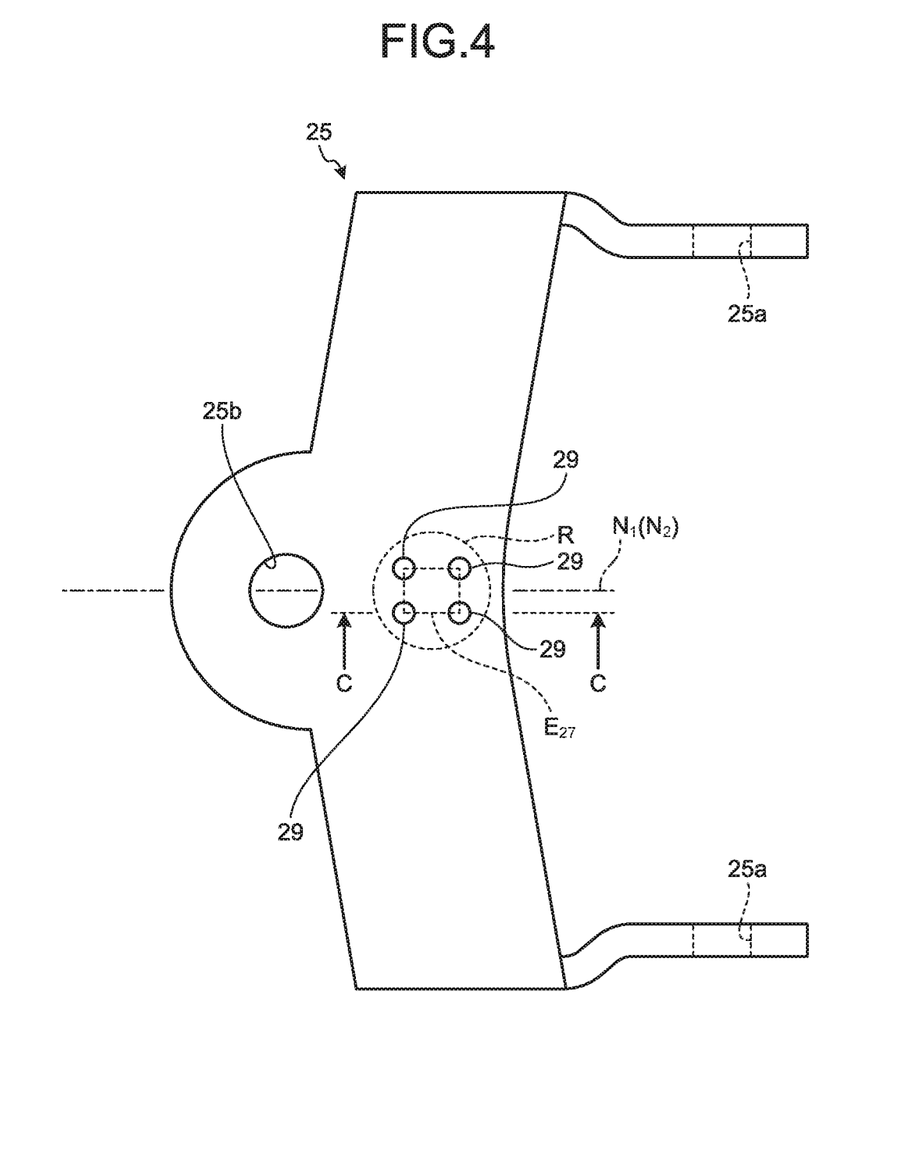
FIG. 4 is a plan view illustrating the configuration of the main components of the endoscope according to the embodiment.

FIG. 4 is a plan view illustrating the configuration of main components of the endoscope according to the embodiment and is a plan view illustrating a joint ring 25 when viewed from a direction indicated by an arrow B in FIG. 2. Two connection holes 25a provided on one end side of the joint ring 25 in a direction of a central axis $N_1$ and two connection hole 25b (only one side illustrated in FIG. 4) provided on the other end side in the direction of the central axis $N_1$ are formed in the joint ring 25. Each of the connection holes 25a and 25b penetrates the joint ring 25 in a direction perpendicular to the central axis $N_1$. The two connection holes 25a are formed on sides opposite to each other in the central axis $N_1$. Similar to the connection holes 25a, the two connection holes 25b are formed on sides opposite to each other in the central axis $N_1$. Each of the connection holes 25a and 25b is formed at a position shifted around the central axis by 90°. The connection holes 25a are located closer to the inner circumferential side of the joint ring 25 than the connection holes 25b.

Regarding two joint rings 25 adjacent to each other in the longitudinal direction, as illustrated in FIG. 2, a rivet 28 is inserted into a hole formed by aligning the connection hole 25a of the one joint ring 25 and the connection hole 25b of the other joint ring 25, and thus the joint rings 25 adjacent to each other are connected to be rotatable around the central axis of the rivet 28. At this time, one joint ring 25 of two joint rings 25 adjacent to each other in the direction of the central axis $N_1$ is rotated around the central axis $N_1$ by 90° with respect to the other joint ring 25. Thus, the connection hole 25a of the one joint ring 25 overlaps the connection hole 25b of the other joint ring 25.

An operation wire 26 that connects the operating unit 3 and the bending unit 22 to each other and is used for operating the bending unit 22 is inserted into the insertion portion 2. The operation wire 26 has a line-like shape. The operation wire 26 is inserted into a wire holder 27. One end of the operation wire 26 is fixed to a bending piece on the distal end side of the bending unit 22, and the other end of the operation wire 26 is fixed to the operating unit 3. The operation wire 26 is configured with a stranded wire formed by bundling a plurality of strands or with one strand. If a user operates the operating unit 3 (for example, the above-described curved knob), the operation wire 26 moves back and forth, and the bending unit 22 bends by the back-and-forth movement (see broken line in FIG. 1).

In the bending unit 22, the operation wire 26 is guided by the wire holder 27. The wire holder 27 is fixed to any of the plurality of joint rings 25 (see FIG. 2). At least one wire holder 27 is provided for each operation wire 26 inserted into the insertion portion 2. That is, each operation wire 26 is inserted into at least one wire holder 27 in the bending unit 22.

The wire holder 27 is formed of metal and has a tubular shape having an outer diameter which is smaller than the inner diameter of the joint ring 25. The wire holder 27 has an inner diameter allowing the operation wire 26 to be inserted into the wire holder 27. The length of the wire holder 27 in a direction of the central axis $N_2$ is smaller than the length of the joint ring 25 in the direction of the central axis $N_1$. In the embodiment, the central axis $N_1$ and the central axis $N_2$ are parallel to each other.

The wire holder 27 is fixed to the inner circumferential side of the joint ring 25 by welding. A welded portion 29 is formed in the joint ring 25 and the wire holder 27 in a manner that portions of the joint ring 25 and the wire holder 27 are melted and solidified by welding. In the embodiment, four welded portions 29 are formed with respect to the wire holder 27. The welded portion 29 is formed, for example, by spot welding with a laser beam, and has a spot shape on the outer surface of the joint ring 25.

Figure 5:
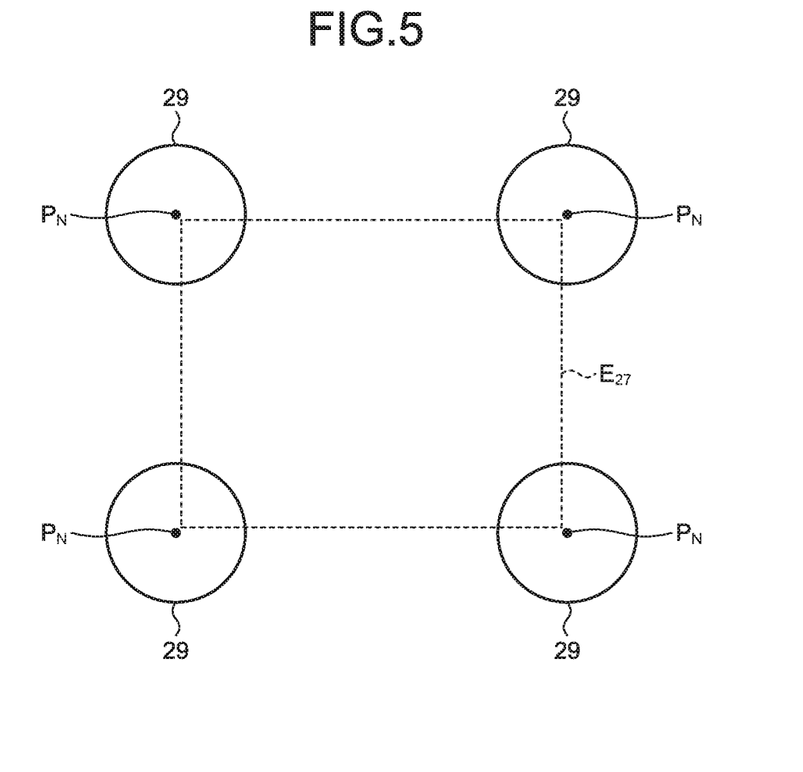
FIG. 5 is an enlarged view of a region R illustrated in FIG. 4.

FIG. 5 is an enlarged view of a region R illustrated in FIG. 4. The welded portions 29 are provided at positions including corners of a projection region $E_{27}$ of the wire holder 27 when the wire holder 27 disposed on the inner circumferential side of the joint ring 25 is projected onto the outer surface of the joint ring 25, respectively. The projection region $E_{27}$ is a region when the wire holder 27 is projected onto the outer surface of the joint ring 25 in a direction which is perpendicular to the central axis $N_1$ of the joint ring 25 and is along an axis passing through the central axis $N_1$ and the central axis $N_2$ of the wire holder 27. The projection region $E_{27}$ has a rectangular shape constituting four edges forming an outer edge. The corner of the projection region $E_{27}$ is located at a position at which the edges cross each other. A welding center $P_N$ of the welded portion 29 on the outer surface of the joint ring 25 is located on an outside of the projection region $E_{27}$. Here, the welding center $P_N$ corresponds to a position through which an optical axis of laser light in welding passes and corresponds to a center position of a melted trace. Here, the welded portion 29 refers to the entire melted-solidified portion. A weld mark refers to a trace of welding appearing on the surface of the joint ring 25.

Figure 6:
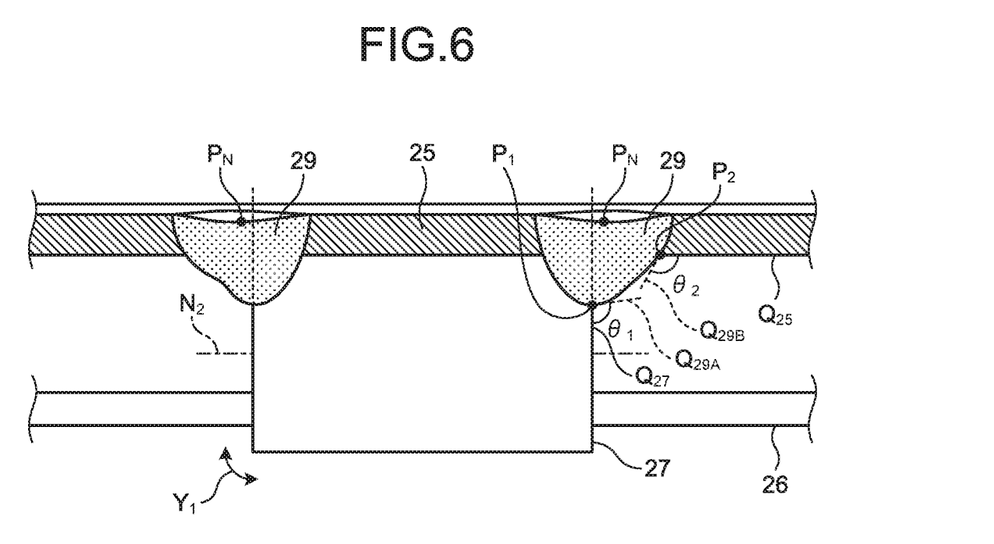
FIG. 6 is a sectional view taken along C-C in FIG. 4.

FIG. 6 is a sectional view taken along C-C in FIG. 4. FIG. 6 is a sectional view taken along a plane which is parallel to a plane including the central axis $N_1$ (see FIG. 2) of the joint ring 25 and the central axis $N_2$ of the wire holder 27 and is a plane passing through the welding center $P_N$ of the outer surface of the welded portion 29. In the section, a contact angle $\theta_1$ is an obtuse angle ($90° < \theta_1 < 180°$). The contact angle is an angle formed by a tangent line $Q_{29A}$ of the welded portion 29 at an intersection point $P_1$ between the welded portion 29 and an end surface of the wire holder 27 and a straight line $Q_{27}$ extending along the end surface of the wire holder 27.

In the above-described plane (plane which is parallel to the plane including the central axis $N_1$ and the central axis $N_2$ and passes through the welding center $P_N$ of the welded portion 29 on the outer surface), a contact angle $\theta_2$ is an obtuse angle ($90° < \theta_2 < 180°$). The contact angle $\theta_2$ is an angle formed by a tangent line $Q_{29B}$ of the welded portion 29 at an intersection point $P_2$ between the welded portion 29 and the inner circumferential surface of the joint ring 25 and a straight line $Q_{25}$ extending along the inner circumferential surface of the joint ring 25.

The welded portion 29 has a curved surface having a surface which smoothly continues from the inner circumferential surface side of the joint ring 25 to the end surface of the wire holder 27, for example, a spline curved surface. As illustrated in FIG. 6, a curve connecting the intersection points $P_1$ and $P_2$ along the surface of the welded portion 29 has a smooth arc shape. The welded portion 29 reaches the inner circumferential surface of the wire holder 27.

Figure 7:
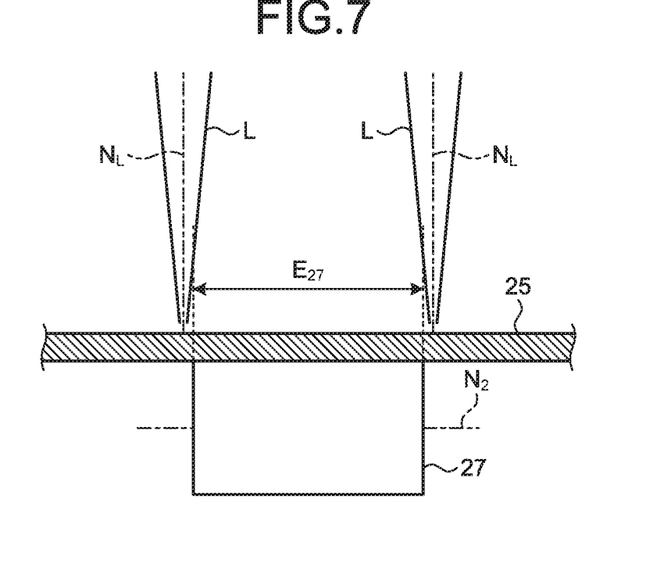
FIG. 7 is a diagram illustrating welding between the joint ring and the wire holder in the endoscope according to the embodiment.

Next, a method of bonding the above-described wire holder 27 to the joint ring 25 will be described with reference to FIG. 7. FIG. 7 is a diagram illustrating welding between the joint ring and the wire holder of the endoscope according to the embodiment and is a sectional view illustrating a portion of the joint ring 25, which corresponds to the C-C section in FIG. 4 and the wire holder 27.

Firstly, the wire holder 27 is positioned with respect to the inner circumference of the joint ring 25. At this time, if the wire holder 27 is brought into close contact with the inner circumferential surface of the joint ring 25 by using an actuator such as an air cylinder or a collet chuck, this is preferable from a point that it is possible to fix the position of the wire holder 27 to the joint ring 25.

After the wire holder 27 is positioned with respect to the inner circumference of the joint ring 25, irradiation with laser light L is performed from the outer surface of the joint ring 25, and thus the wire holder 27 is fixed to the joint ring 25. An optical axis $N_L$ of the laser light L is located on the outside of the projection region $E_{27}$ of the wire holder 27 as described above (for example, see FIG. 7). In a case illustrated in FIG. 7, the optical axis $N_L$ of the laser light L is located on the outside of the above-described projection region $E_{27}$. If the irradiation with the laser light L is performed, a portion of the joint ring 25 and a portion of the wire holder 27 are welded. At this time, a melted portion of the joint ring 25 flows into a space formed between the joint ring 25 and the wire holder 27. If the irradiation with laser light L is stopped, and the melted portion is cooled, the melted portion of the joint ring 25 and the melted portion of the wire holder 27 are solidified, and thereby the welded portion 29 is formed (for example, see FIG. 6). The welding center $P_N$ of the welded portion 29 formed in this manner is located on the outside of the projection region $E_{27}$ (see FIG. 5).

Regarding the laser light L used for forming the welded portion 29, an oscillation cycle may be controlled in nanoseconds to several seconds. The welded portion 29 may be formed by one laser irradiation, or may be formed by plural number of times of irradiations. The laser light L is preferably generated using a device capable of controlling the irradiation area, such as a fiber laser, from the viewpoint of controlling the welding position and the welding area.

In the above-described embodiment, the joint ring 25 and the wire holder 27 are bonded to each other in a manner that the welded portion 29 is formed at a position including the corner of the projection region $E_{27}$ obtained by projecting the wire holder 27 onto the outer surface of the joint ring 25, by melting and solidifying a portion of the joint ring 25 and a portion of the wire holder 27. In the embodiment, welding may be performed even though a space is provided between the joint ring 25 and the wire holder 27. Thus, processing of aligning the wire holder 27 on the inner circumferential surface of the joint ring 25 is not required. It is possible to improve strength against flap (arrow $Y_1$ in FIG. 6) in the direction of the central axis $N_2$ or flap (arrow $Y_2$ in FIG. 3) in the direction perpendicular to the central axis $N_2$ occurring by the back-and-forth movement of the operation wire 26. In particular, since the strength against the flap in the direction of the central axis $N_2$, which increases when the operation wire 26 moves back and forth, it is possible to maintain fixation between the joint ring 25 and the wire holder 27. According to the embodiment, it is possible to suppress an increase of an outer diameter of the joint ring 25 and to improve strength against flap in the wire insertion direction. As a result, it is possible to maintain operability of the operation wire 26 or the fixed state between the joint ring 25 and the wire holder 27 more reliably. Here, the term "flap" means, for example, that the wire holder 27 rotates in a direction in which the central axis $N_2$ is inclined in a plane including the central axis $N_2$.

For example, in a case where the wire holder 27 having an inner diameter of ϕ0.4 mm and a thickness of 0.2 mm is welded to the joint ring 25 having an inner diameter of ϕ5 mm and a thickness of 0.12 mm as illustrated in FIG. 6, the strength against the flap (arrow $Y_1$ in FIG. 6) in the direction of the central axis $N_2$ is about 90 N. In the welding, laser light emitted from multimode fiber is used under conditions of a laser output of 93 W and a pulse width of 10 ms. In a case where four welded portions 29 are similarly formed within the above-described projection region $E_{27}$, by using the same joint ring 25 and the same wire holder 27, and then are welded, the strength against the flap (arrow $Y_1$ in FIG. 6) in the direction of the central axis $N_2$ is about 60 N. Thus, it is understood that it is possible to improve strength against flap by performing welding on the outside of the projection region $E_{27}$ as in the embodiment.

According to the above-described embodiment, the welded portion 29 is formed by spot welding. Thus, it is possible to form the welded portion 29 with the minimum heat energy necessary for welding, and thus to suppress an occurrence of a situation in which the joint ring 25 or the wire holder 27 around the welded portion 29 is deteriorated by the excess thermal energy.

In the above-described embodiment, descriptions are made on the assumption that the welded portion 29 reaches the inner circumferential surface of the wire holder 27. However, the welded portion 29 may not reach the inner circumferential surface of the wire holder 27.

First Modification Example of Embodiment

Figure 8:
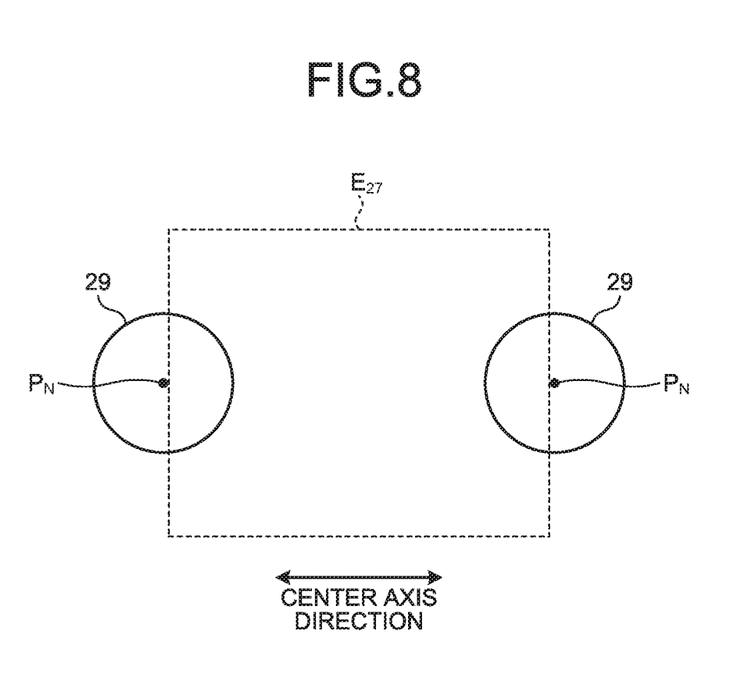
FIG. 8 is a schematic diagram illustrating a configuration of main components of an endoscope according to a first modification example of the embodiment.

FIG. 8 is a schematic diagram illustrating a configuration of main components of an endoscope according to a first modification example of the embodiment. In the first modification example, two welded portions 29 are formed in a direction parallel to the central axis $N_2$.

In the first modification example, the welded portions 29 are formed at center portions of the edges crossing the central axis $N_2$ among four edges of the wire holder 27, which constitute an outer edge of the projection region $E_{27}$, respectively. Even in the first modification example, the welding center $P_N$ of the surface of the welded portion 29 on the outer surface of the joint ring 25 is located on an outside of the projection region $E_{27}$. Similar to the embodiment, the contact angles $\theta_1$ and $\theta_2$ are obtuse angles.

In the above-described first modification example, the two welded portions 29 are formed in the direction of the central axis $N_2$. Thus, it is possible to secure strength against flap (arrow $Y_1$ in FIG. 6) in the direction of the central axis $N_2$ occurring by the back-and-forth movement of the operation wire 26 and to fix the joint ring 25 and the wire holder 27 to each other.

Second Modification Example of Embodiment

Figure 9:
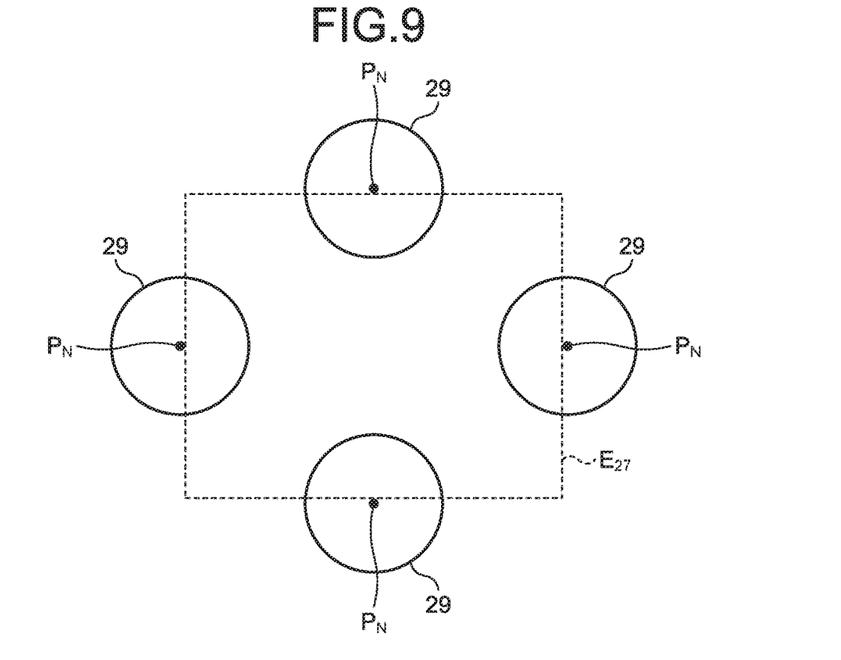
FIG. 9 is a schematic diagram illustrating a configuration of main components of an endoscope according to a second modification example of the embodiment.

FIG. 9 is a schematic diagram illustrating a configuration of main components of an endoscope according to a second modification example of the embodiment. In the second modification example, a welded portion 29 is formed at the center portion of each side of a rectangular boundary that constitutes an outer edge of the projection region $E_{27}$.

Even in the second modification example, the welding center $P_N$ of the surface of the welded portion 29 on the outer surface of the joint ring 25 is located on an outside of the projection region $E_{27}$. Similar to the embodiment, the contact angles $\theta_1$ and $\theta_2$ are obtuse angles.

In the above-described second modification example, the welded portion 29 is formed at the center portion of each side of the rectangular boundary that constitutes the outer edge of the projection region $E_{27}$. Thus, it is possible to secure strength against flap (arrow $Y_1$ in FIG. 6) in the direction of the central axis $N_2$ or flap (arrow $Y_2$ in FIG. 3) in the direction perpendicular to the central axis $N_2$ occurring by the back-and-forth movement of the operation wire 26, and to fix the joint ring 25 and the wire holder 27 to each other.

Third Modification Example of Embodiment

Figure 10:
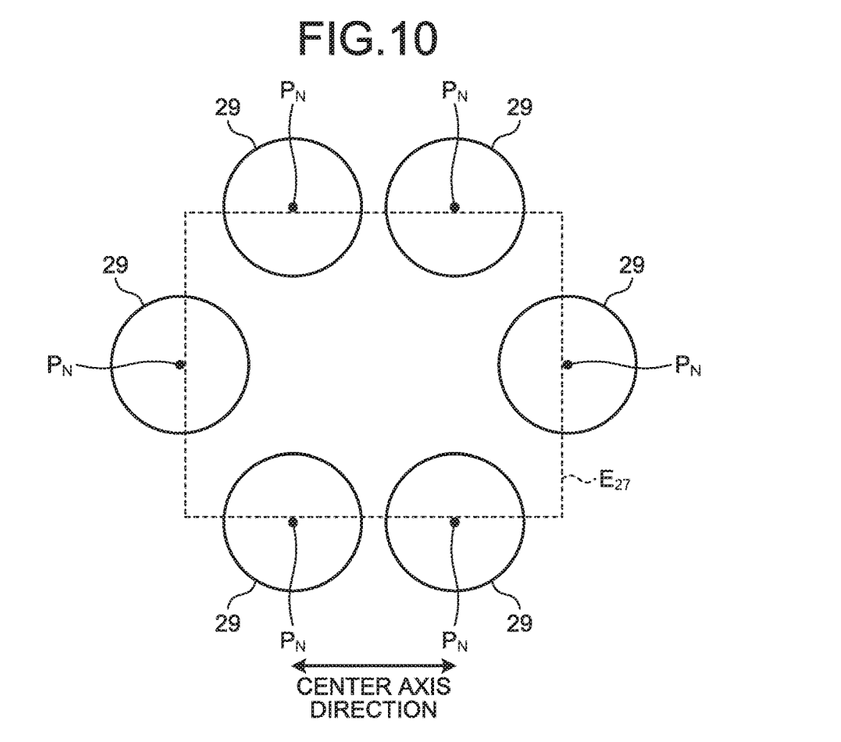
FIG. 10 is a schematic diagram illustrating a configuration of main components of an endoscope according to a third modification example of the embodiment.

FIG. 10 is a schematic diagram illustrating a configuration of main components of an endoscope according to a third modification example of the embodiment. In the third modification example, one or two welded portions 29 are formed on each side of a rectangular boundary constituting an outer edge of the projection region $E_{27}$.

In the third modification example, the welded portion 29 is provided on each side of the rectangular boundary constituting an outer edge of the projection region $E_{27}$ of the wire holder 27. Specifically, one welded portion 29 is provided at the center portion of each side of a set of sides crossing the direction of the central axis $N_2$. Two welded portions 29 are provided on a set of sides parallel to the central axis $N_2$, respectively. Even in the third modification example, the welding center $P_N$ of the surface of the welded portion 29 on the outer surface of the joint ring 25 is located on an outside of the projection region $E_{27}$. Similar to the embodiment, the contact angles $\theta_1$ and $\theta_2$ are obtuse angles.

In the above-described third modification example, the one or two welded portions 29 are formed on each side of the rectangular boundary constituting the outer edge of the projection region $E_{27}$. Thus, it is possible to secure strength against flap (arrow $Y_1$ in FIG. 6) in the direction of the central axis $N_2$ or flap (arrow $Y_2$ in FIG. 3) in the direction perpendicular to the central axis $N_2$ occurring by the back-and-forth movement of the operation wire 26, and to fix the joint ring 25 and the wire holder 27 to each other.

Fourth Modification Example of Embodiment

Figure 11:
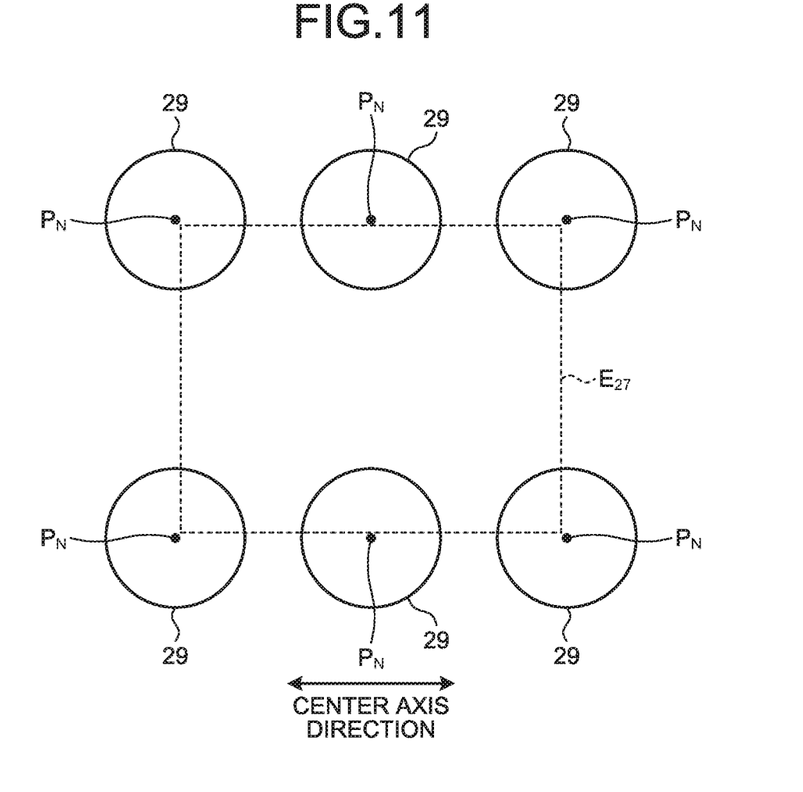
FIG. 11 is a schematic diagram illustrating a configuration of main components of an endoscope according to a fourth modification example of the embodiment.

FIG. 11 is a schematic diagram illustrating a configuration of main components of an endoscope according to a fourth modification example of the embodiment. In the fourth modification example, a welded portion 29 is formed at each corner of a rectangular boundary constituting an outer edge of the projection region $E_{27}$, and at center portions of a set of sides parallel to the central axis $N_2$ of the wire holder 27.

Even in the fourth modification example, the welding center $P_N$ of the surface of the welded portion 29 on the outer surface of the joint ring 25 is located on an outside of the projection region $E_{27}$. Similar to the embodiment, the contact angles $\theta_1$ and $\theta_2$ are obtuse angles.

In the above-described fourth modification example, the welded portion 29 is formed at each corner of the boundary constituting the outer edge of the projection region $E_{27}$, and at the center portions of the set of sides parallel to the central axis $N_2$. Thus, it is possible to secure strength against flap (arrow $Y_1$ in FIG. 6) in the direction of the central axis $N_2$ or flap (arrow $Y_2$ in FIG. 3) in the direction perpendicular to the central axis $N_2$ occurring by the back-and-forth movement of the operation wire 26, and to fix the joint ring 25 and the wire holder 27 to each other.

Hitherto, although the embodiments for carrying out the present disclosure have been described above, the present disclosure is not limited only by the above-described embodiment. For example, in the above-described embodiment, the configuration of the endoscope has been described. However, the present disclosure may be applied to any bending device such as a manipulator, in which a bending structure using the joint ring and the wire holder is provided at a distal end.

In the above-described embodiment and modification examples, descriptions are made on the assumption that the welding center $P_N$ of the welded portion 29 is located out of the projection region $E_{27}$. However, the welding center $P_N$ may be located within the projection region $E_{27}$. It is possible to obtain the above-described effects so long as a portion of a region for forming the welded portion 29 is out of the projection region $E_{27}$.

Regarding the plurality of welded portions 29 according to the above-described embodiment and modification examples, shapes and sizes of all or some of the welded portions 29 may be different from each other. As in the third modification example or the fourth modification example, in a case where the plurality of welded portions 29 is formed along the central axis $N_2$, the welded portions 29 adjacent to each other may overlap each other.

In the above-described embodiment and modification examples, descriptions are made on the assumption that laser welding with laser light is performed. However, the welding method is not limited thereto. For example, it is also possible to use well-known welding techniques such as electron beam welding.

As described above, the present disclosure may include various embodiments in a range without departing from the technical concept described in the claims.

As described above, the welded structure of the tubular member and the bending device according to the present disclosure are useful for suppressing an increase of the outer diameter of the joint ring and improving the strength against flap in the wire insertion direction.

According to the present disclosure, effects that it is possible to suppress an increase of an outer diameter of the joint ring and to improve strength against flap in a wire insertion direction are exhibited.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A welded structure comprising:
 a first tube made of metal, the first tube extending in a longitudinal direction;
 a second tube welded to an inner circumferential surface of the first tube, the second tube being made of metal, the second tube having an outer diameter smaller than an inner diameter of the first tube and having first and second end surfaces separated in the longitudinal direction; and a plurality of welds at which a first portion of the first tube and a second portion of the second tube are melted and solidified, a surface melted and solidified from the inner circumferential surface of the first tube toward one or more of the first and second end surfaces of the second tube forms a smoothly-continuous curved surface to bond the first tube and the second tube to each other, wherein at least a portion of each of the plurality of welds is located on an outer surface of the first tube outside of a projection of the second tube onto the first tube in a radial direction of the first tube.

2. The welded structure according to claim 1, wherein each of the plurality of welds has a spot shape on the outer surface of the first tube, and wherein a center of each of the plurality of welds is located on the outer surface of the first tube outside of the projection.

3. The welded structure according to claim 1, wherein in a cross section of the first tube and the second tube viewed in a plane including a first central axis of the first tube and a second central axis of the second tube, an angle between a tangent line of each of the plurality of welds at an intersection point and a straight line is an obtuse angle, the intersection point being between each of the plurality of welds and one or more of the first and second end surfaces in the longitudinal direction, and the straight line extending along the one or more of the first and second end surfaces.

4. The welded structure according to claim 3, wherein, in the cross section, an angle between a tangent line of each of the plurality of welds at an intersection point and a straight line is an obtuse angle, the intersection point being between each of the plurality of welds and the inner circumferential surface of the first tube, and the straight line extending along the inner circumferential surface of the first tube.

5. The welded structure according to claim 1, wherein a center of a melted trace on the outer surface of the first tube at each of the plurality of welds is located outside of the projection.

6. The welded structure of claim 1, wherein a longitudinal length of the second tube is shorter than a longitudinal length of the first tube.

7. The welded structure of claim 1, wherein the first tube is a joint ring for a bending portion of an endoscope.

8. The welded structure of claim 7, wherein the second tube is a wire holder for accommodating a bending wire for operation of the bending portion.

9. A bending portion for use in an insertion portion of an endoscope, the bending portion comprising:

a bending portion comprising a plurality of joint rings rotatable connected relative to each other;

at least one joint ring of the plurality of joint rings being made of metal, the at least one joint ring extending in a longitudinal direction;

at least one wire holder configured to accommodate a bending wire for operation of the bending portion, the at least one wire holder being welded to an inner circumferential surface of the at least one joint ring, the at least one wire holder being made of metal, the at least one wire holder having an outer diameter smaller than an inner diameter of the at least one joint ring and having first and second end surfaces separated in the longitudinal direction; and a plurality of welds at which a first portion of the at least one joint ring and a second portion of the at least one wire holder are melted and solidified, a surface melted and solidified from the inner circumferential surface of the at least one joint ring toward one or more of the first and second end surfaces of the at least one wire holder forms a smoothly-continuous curved surface to bond the at least one joint ring and the at least one wire holder to each other, wherein at least a portion of each of the plurality of welds is located on an outer surface of the at least one joint ring outside a projection of the at least one wire holder onto the at least one joint ring in a radial direction of the at least one joint ring.

10. The bending portion according to claim 9, wherein each of the plurality of welds has a spot shape on the outer surface of the at least one joint ring, and wherein a center of each of the plurality of welds is located on the outer surface of the at least one joint ring outside of the projection.

11. The bending portion according to claim 9, wherein in a cross section of the at least one joint ring and the at least one wire holder viewed in a plane including a first central axis of the at least one joint ring and a second central axis of the at least one wire holder, an angle between a tangent line of each of the plurality of welds at an intersection point and a straight line is an obtuse angle, the intersection point being between each of the plurality of welds and one or more of the first and second end surfaces in the longitudinal direction, and the straight line extending along the one or more of the first and second end surfaces.

12. The bending portion according to claim 11, wherein, in the cross section, an angle between a tangent line of each of the plurality of welds at an intersection point and a straight line is an obtuse angle, the intersection point being between each of the plurality of welds and the inner circumferential surface of the at least one joint ring, and the straight line extending along the inner circumferential surface of the at least one joint ring.

13. The bending portion according to claim 9, wherein a center of a melted trace on the outer surface of the at least one joint ring at each of the plurality of welds is located outside of the projection.

14. The bending portion of claim 9, wherein a longitudinal length of the at least one wire holder is shorter than a longitudinal length of the at least one joint ring.

* * * * *